(12) United States Patent
Meshberg

(10) Patent No.: US 10,384,022 B2
(45) Date of Patent: Aug. 20, 2019

(54) HAND-HELD DOSE-DISPENSING PRESSURIZED SPRAY INHALER WITH CHILD RESTRAINT CAPABILITY

(71) Applicant: Emil Meshberg, Fairfield, CT (US)

(72) Inventor: Emil Meshberg, Fairfield, CT (US)

(73) Assignee: PACKAGING CONCEPTS ASSOCIATES HOLDINGS, INC., Torrington, CT (US)

( * ) Notice: Subject to any disclaimer, the term of this patent is extended or adjusted under 35 U.S.C. 154(b) by 0 days.

(21) Appl. No.: 15/428,714

(22) Filed: Feb. 9, 2017

(65) Prior Publication Data

US 2018/0221601 A1    Aug. 9, 2018

(51) Int. Cl.
*A61M 15/00*    (2006.01)

(52) U.S. Cl.
CPC ...... *A61M 15/009* (2013.01); *A61M 15/0021* (2014.02); *A61M 2205/276* (2013.01)

(58) Field of Classification Search
CPC .... A61M 15/00; A61M 15/009; A61M 11/08; A61M 2205/276
See application file for complete search history.

(56) References Cited

U.S. PATENT DOCUMENTS

| | | | |
|---|---|---|---|
| 4,454,966 A * | 6/1984 | Hicks | A45D 34/02 222/153.11 |
| 5,379,924 A * | 1/1995 | Taylor | B65D 83/205 222/402.11 |
| 5,447,150 A | 9/1995 | Bacon | |
| 5,531,359 A * | 7/1996 | Winner | B65D 83/384 222/153.11 |
| 5,718,355 A | 2/1998 | Garby et al. | |
| 6,792,941 B2 | 9/2004 | Andersson | |
| 6,971,552 B2 * | 12/2005 | Meshberg | B05B 11/3059 222/153.13 |
| 7,743,945 B2 | 6/2010 | Lu et al. | |
| 7,967,011 B2 | 6/2011 | Hodson et al. | |
| 8,357,114 B2 | 1/2013 | Poutiatine et al. | |
| 8,474,448 B2 | 7/2013 | Oi et al. | |
| 8,777,061 B1 * | 7/2014 | Meshberg | B05B 11/3059 222/153.11 |
| 9,205,445 B2 * | 12/2015 | Fang | B05B 17/0607 |
| 9,821,127 B2 * | 11/2017 | Barber | A61M 11/006 |
| 9,835,279 B2 * | 12/2017 | Plumptre | F16L 55/00 |

(Continued)

*Primary Examiner* — LaToya M Louis
(74) *Attorney, Agent, or Firm* — Glenn E. Gold, P.A.; Glenn E. Gold

(57) ABSTRACT

A hand-held dose-dispensing pressurized spray inhaler includes a housing, an aerosol canister in the housing having a canister body and a movable valve stem biased to extend therefrom, a fixture stationarily supporting the valve stem relative to the housing, and an actuation mechanism partially fitting over the canister body opposite from the valve stem such that only together with the fixture the canister body is supported in the housing with a clearance gap between the canister body and the housing and for movement relative to the housing and toward and away from the valve stem and fixture. The actuation mechanism provides a child restraint capability requiring two unlocking actions be carried out to convert it from a locked to an unlocked condition before it can move the canister body relative to the housing and valve stem to release a dose of pressurized spray from the valve stem.

3 Claims, 8 Drawing Sheets

(56) References Cited

U.S. PATENT DOCUMENTS

| | | | |
|---|---|---|---|
| 2002/0000225 A1 | 1/2002 | Schuler et al. | |
| 2004/0094147 A1 | 5/2004 | Schyra et al. | |
| 2004/0221840 A1* | 11/2004 | Stockman-Lamb | A61J 7/0472 128/200.23 |
| 2004/0231667 A1* | 11/2004 | Horton | A61M 15/0065 128/202.13 |
| 2006/0151536 A1 | 7/2006 | Wong et al. | |
| 2009/0183744 A1 | 7/2009 | Hayton et al. | |
| 2010/0192946 A1* | 8/2010 | Oi | A61M 15/009 128/200.23 |
| 2012/0006322 A1* | 1/2012 | Anderson | A61M 15/009 128/200.23 |
| 2013/0056888 A1* | 3/2013 | Holakovsky | A61M 15/0065 261/78.2 |
| 2015/0328651 A1* | 11/2015 | Hohmann | B05B 11/3059 604/192 |
| 2015/0335528 A1* | 11/2015 | Kim | A61H 35/04 128/200.17 |

* cited by examiner

HAND-HELD DOSE-DISPENSING PRESSURIZED SPRAY INHALER WITH CHILD RESTRAINT CAPABILITY

FIELD OF THE INVENTION

The present invention relates to hand-held dispensing devices, and, more particularly, is concerned with a hand-held dose-dispensing apparatus having child restraint capabilities that can deliver aerosol and/or non-aerosol based substances.

BACKGROUND OF THE INVENTION

In the case of certain medicinal substances, such as inhaled spray formulations, it may be desirable that an inhaler be provided with child restraint features to prevent operation of its dispensing mechanism by a child or accidental operation in general, for example when carrying the inhaler in a pocket or handbag. While it may be desirable that the inhaler be provided with child restraint features, it nevertheless may also be desirable that, at the same time, the operation of the inhaler be simple for adults to operate, especially elderly people. This is particularly important in the case of inhalers for medicinal substances, where it is desirable to simplify how to use the inhaler in order to minimize potential confusion and enable correct operation of the inhaler.

Thus, in the design of hand-held inhalers the developer must strive to achieve a balance between these competing desirable features. This is particularly the case when another, overriding, design feature is that the specific design of the haler be one which is compact, portable and lends itself to mass production.

Accordingly, there remains a need in the art for an innovation that will overcome deficiencies and problems that remain unsolved.

SUMMARY OF THE INVENTION

The present invention is directed to an innovation that overcomes the deficiencies of the known art and the problems that remain unsolved by providing a hand-held dose-dispensing pressurized spray inhaler that incorporates a simple, compact and reliable actuation mechanism that lends itself to both mass production and child restraint capability.

In one aspect of the present invention, a hand-held dose-dispensing pressurized spray inhaler includes:
a housing having an interior chamber;
an aerosol canister disposed in the interior chamber of the housing and having a canister body and a movable valve stem biased to extend from the canister body and retract against the bias toward the canister body to produce release of a dose of pressurized spray from the canister body through a dispensing end of the valve stem;
a fixture for stationarily supporting the valve stem relative to the housing; and
an actuation mechanism normally in a locked condition and being convertible to an unlocked condition, the actuation mechanism fitting at least partially over the canister body opposite from the valve stem such that only the actuation mechanism together with the fixture support the canister body in the housing with a clearance gap around and between the canister body and the housing and for movement relative to the housing and toward and away from the fixture, the actuation mechanism providing a child restraint capability by requiring that a coordinated sequence of multiple unlocking actions be carried out to convert the actuation mechanism from the locked condition to the unlocked condition and move the canister body relative to the housing and the valve stem in a manner that releases a dose of pressurized spray from the dispensing end of the valve stem and from the housing.

In another aspect of the present invention, the housing comprises:
a housing body;
a pair of opposite open ends on the housing body, the interior chamber extending through the housing body between the opposite open ends; and
a mouthpiece on the housing body at one of the opposite open ends thereof, the mouthpiece extending at an angle to the housing body and having a pair of opposite end openings and an interior passage extending between the opposite end openings so as to provide an extension of the interior chamber of the housing.

In another aspect of the present invention, the fixture has an orifice aligned with the dispensing end of the valve stem of the aerosol canister. The fixture is affixed on the mouthpiece adjacent to the one opposite open end of the housing body. The fixture is a tubular pedestal having an orifice defined on a side thereof and a central passageway leading from the valve stem of the aerosol canister to the orifice.

In another aspect of the present invention, a hand-held dose-dispensing pressurized spray inhaler includes:
a housing of a cylindrical shape and having an interior chamber;
an aerosol canister disposed in the interior chamber of the housing and having a canister body and a movable valve stem biased to extend from the canister body and retract toward the canister body to produce release of a dose of pressurized spray from the canister body through a dispensing end of the valve stem; and
an actuation mechanism normally in a locked condition and being convertible to an unlocked condition, the actuation mechanism comprising
an end cap having an endless side wall of a cylindrical shape conforming to that of the housing and being open at one of a pair of opposite ends of the end cap and having an end wall closing the other of the pair of opposite ends of the end cap and defining an interior cavity in which is partially fitted the canister body at the other of the pair of opposite ends thereof,
a notch made in an end edge of the other opposite open end of the housing body defining a locking edge portion and an unlocking edge portion adjacent to but spaced farther from the end edge than the locking edge portion,
a locking structure formed proximate to and protruding radially outward from an edge portion of the endless side wall of the end cap adjacent the end wall thereof,
an aperture defined in the endless side wall of the cup body adjacent and circumferentially spaced about the endless side wall from the locking structure, and
a yieldable locking member comprising an arcuate ring-shaped segment disposed in the interior cavity of the end cap between the end wall of the end cap and the other opposite end of the canister body and having a outwardly-protruding push button normally projecting through and from the aperture in the endless side wall of the end cap and being depressible into the interior chamber of the housing and within the interior cavity of the end cap for converting the yieldable locking member from a normal locked position to an unlocked position and, while holding the push button so depressed, rotating the end cap with the yieldable locking member and depressed button relative to the housing until the depressed button is confined within the housing in the interior chamber thereof thus allowing depressing of the end cap to cause movement of the canister body relative to the housing toward the valve stem and produce release of the dose of pressurized spray from the canister body through the dispensing end of the valve stem thereof and from the housing.

In another aspect of the present invention, a hand-held dose-dispensing pressurized spray inhaler includes:

a housing having an interior chamber;

an aerosol canister disposed in the interior chamber of the housing and having a canister body and a movable valve stem biased to extend from the canister body and retract toward the canister body to produce release of a dose of pressurized spray from the canister body through a dispensing end of the valve stem;

a fixture for stationarily supporting the valve stem relative to the housing; and an actuation mechanism normally in a locked condition and being convertible to an unlocked condition, the actuation mechanism fitting at least partially over the canister body opposite from the valve stem such that only the actuation mechanism together with the fixture support the canister body in the housing with a clearance gap around and between the canister body and the housing and for movement relative to the housing and toward and away from the fixture, the actuation mechanism providing a child restraint capability by requiring that a coordinated sequence of multiple unlocking actions be carried out to convert the actuation mechanism from the locked condition to the unlocked condition and move the canister body relative to the housing and the valve stem in a manner that releases a dose of pressurized spray from the valve stem and from the housing, wherein the actuation mechanism includes an end cap having an endless side wall of a cylindrical shape conforming to that of the housing body and being open at one of a pair of opposite ends of the end cap and having an end wall closing the other of the pair of opposite ends of the end cap and defining an interior cavity in which is partially fitted the canister body at the other of the pair of opposite ends thereof, a notch made in an end edge of the other opposite open end of the housing body defining a locking edge portion and an unlocking edge portion adjacent to but spaced farther from the end edge than the locking edge portion, a locking structure formed proximate to and protruding radially outward from an edge portion of the endless side wall of the end cap adjacent the end wall thereof, an aperture defined in the endless side wall of the cup body adjacent and circumferentially spaced about the endless side wall from the locking structure, and a yieldable locking member comprising an arcuate ring-shaped segment disposed in the interior cavity of the end cap between the end wall of the end cap and the other opposite end of the canister body and having a outwardly-protruding push button normally projecting through and from the aperture in the endless side wall of the end cap and being depressible into the interior chamber of the housing and within the interior cavity of the end cap for converting the yieldable locking member from a normal locked position to an unlocked position and, while holding the push button so depressed, rotating the end cap with the yieldable locking member and depressed button relative to the housing until the depressed button is confined within the housing in the interior chamber thereof thus allowing depressing of the end cap to cause movement of the canister body relative to the housing toward the valve stem and produce release of the dose of pressurized spray from the canister body through the dispensing end of the valve stem thereof and from the housing.

These and other aspects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, in which.

Like reference numerals refer to like parts throughout the several views of the drawings.

DETAILED DESCRIPTION

Figure 1:
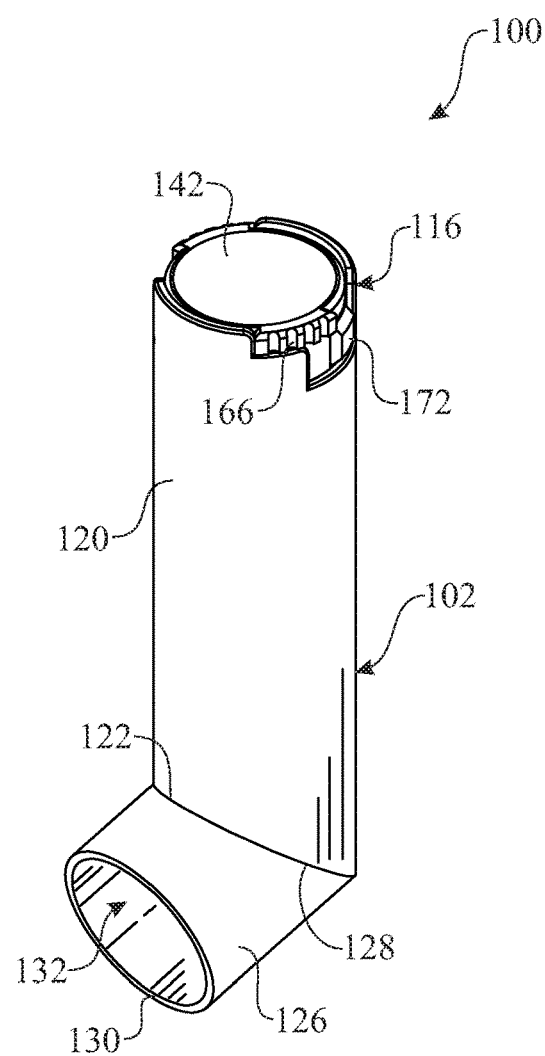
FIG. 1 presents an upper front isometric assembled view of an exemplary embodiment of a hand-held dose-dispensing pressurized spray inhaler in accordance with aspects of the present invention.
Figure 2:
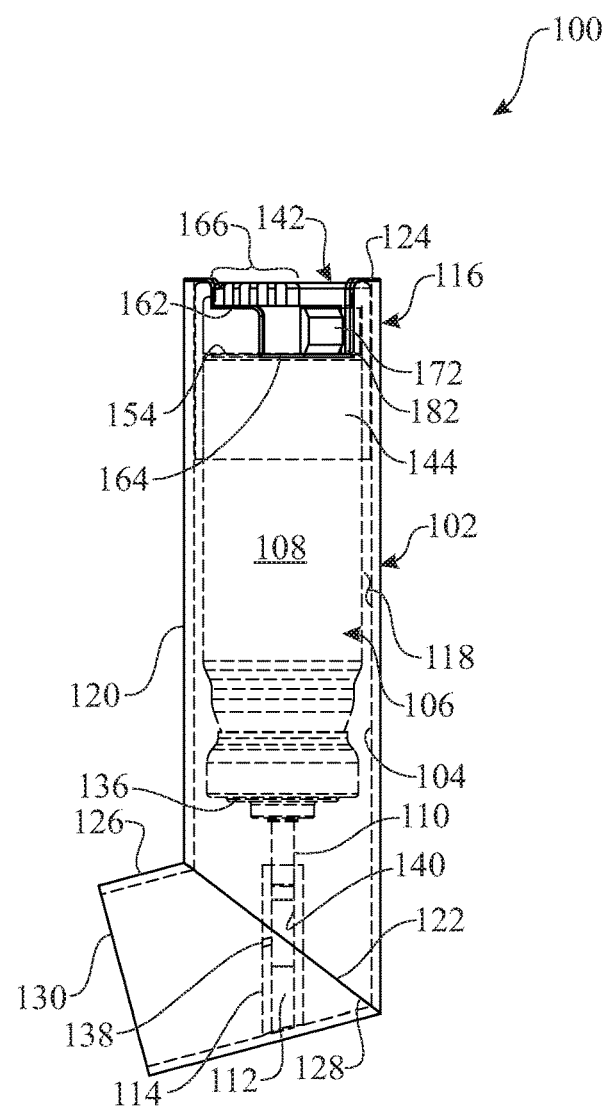
FIG. 2 presents a side elevation assembled view of the dose-dispensing pressurized spray inhaler originally introduced in FIG. 1, illustrating in dashed outline form an aerosol canister containing, for example, the spray formulation under pressure being operatively supported in a housing of the inhaler.
Figure 3:
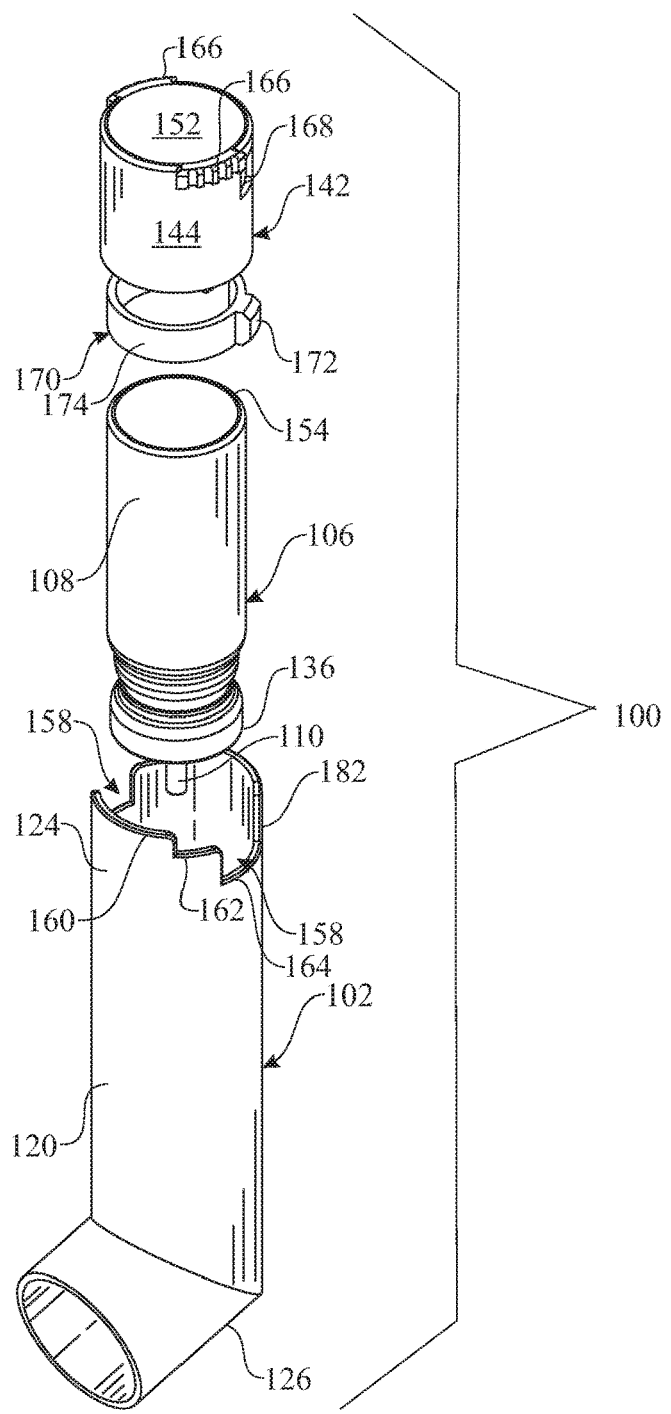
FIG. 3 presents an upper front isometric exploded view of the components of the dose-dispensing pressurized spray inhaler originally introduced in FIG. 1.
Figure 4:
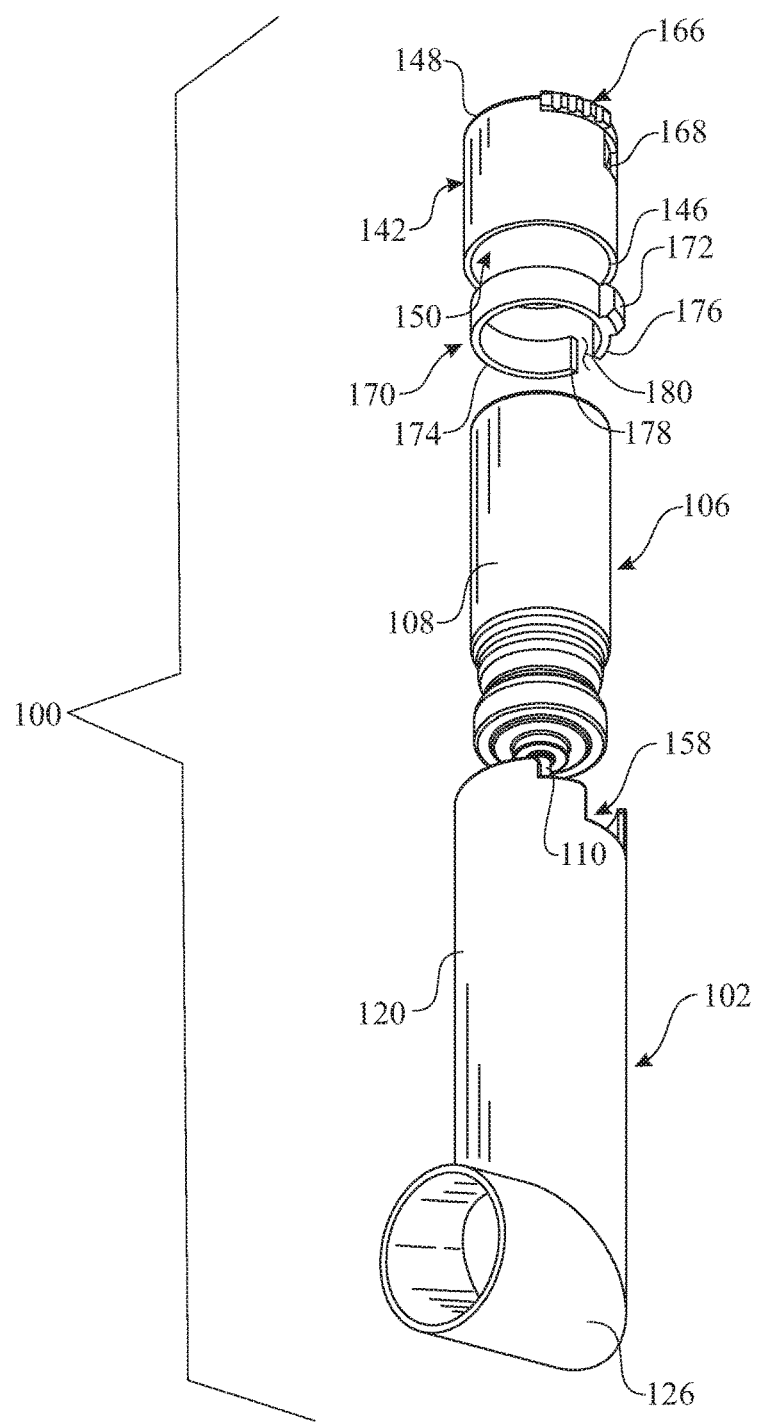
FIG. 4 presents a lower front isometric exploded view of the components of the dose-dispensing pressurized spray inhaler originally introduced in FIG. 1.
Figure 5:
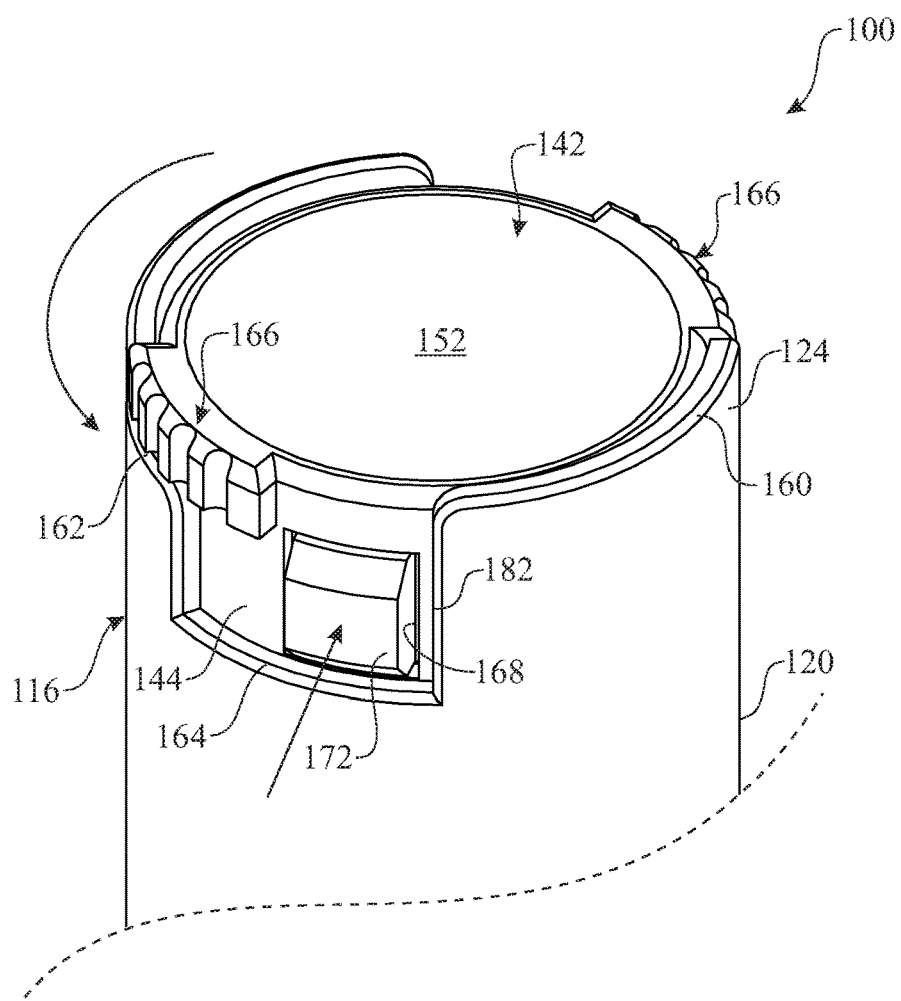
FIG. 5 presents an enlarged fragmentary upper front isometric view of the dose-dispensing pressurized spray inhaler showing an actuation mechanism with child restraint capability in a locked condition with arrows indicating directions of movement of components of the actuation mechanism for converting it to an unlocked condition.
Figure 6:
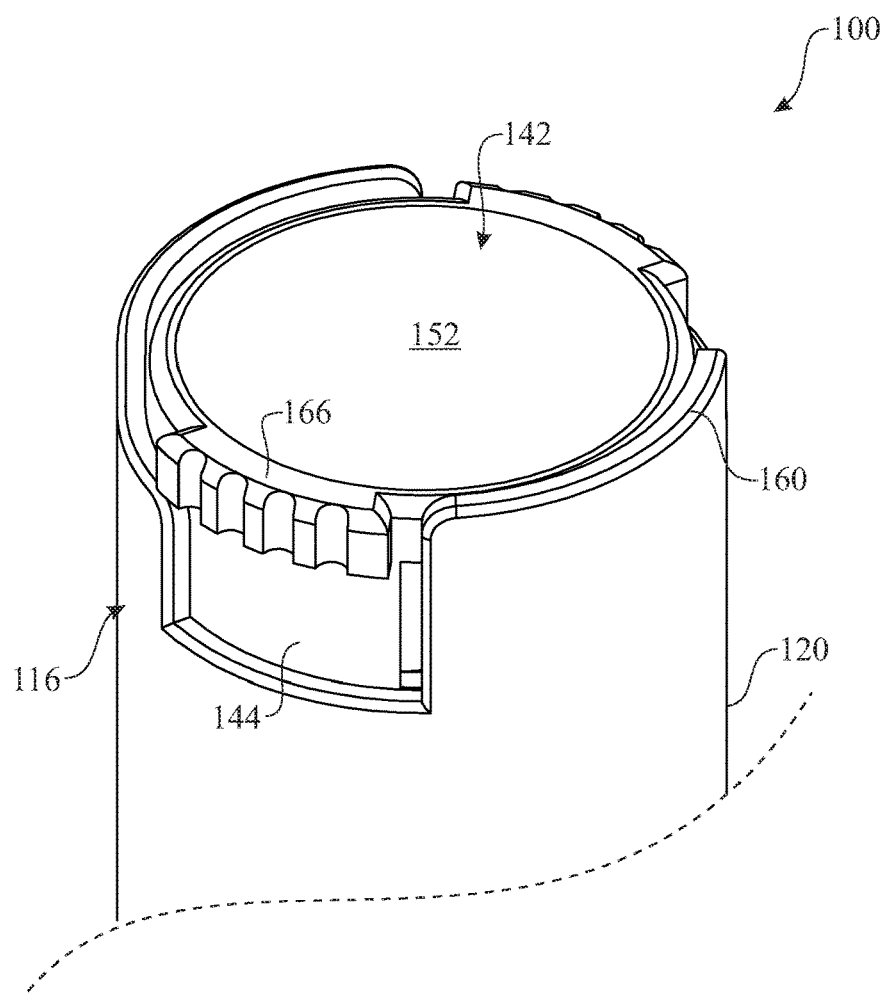
FIG. 6 presents an enlarged fragmentary upper front isometric view of the dose-dispensing pressurized spray inhaler showing the components of the actuation mechanism after conversion to the unlocked condition.
Figure 7:
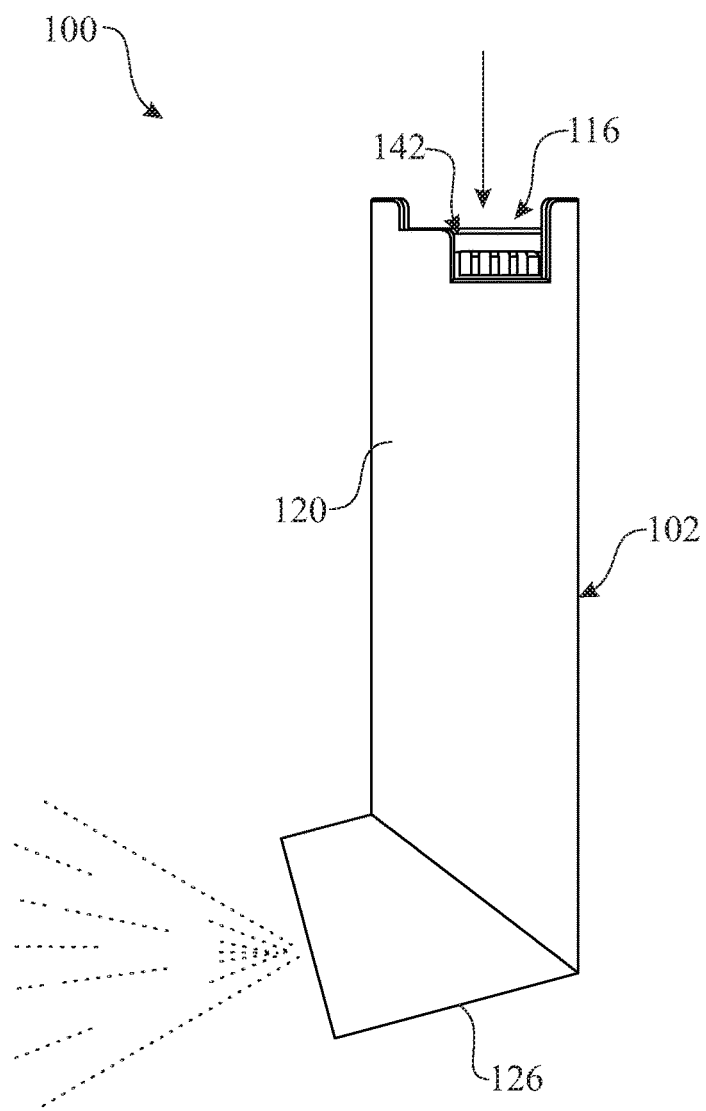
FIG. 7 presents a side elevation view of the dose-dispensing pressurized spray inhaler after being actuated to dispense the spray formulation under pressure.
Figure 8:
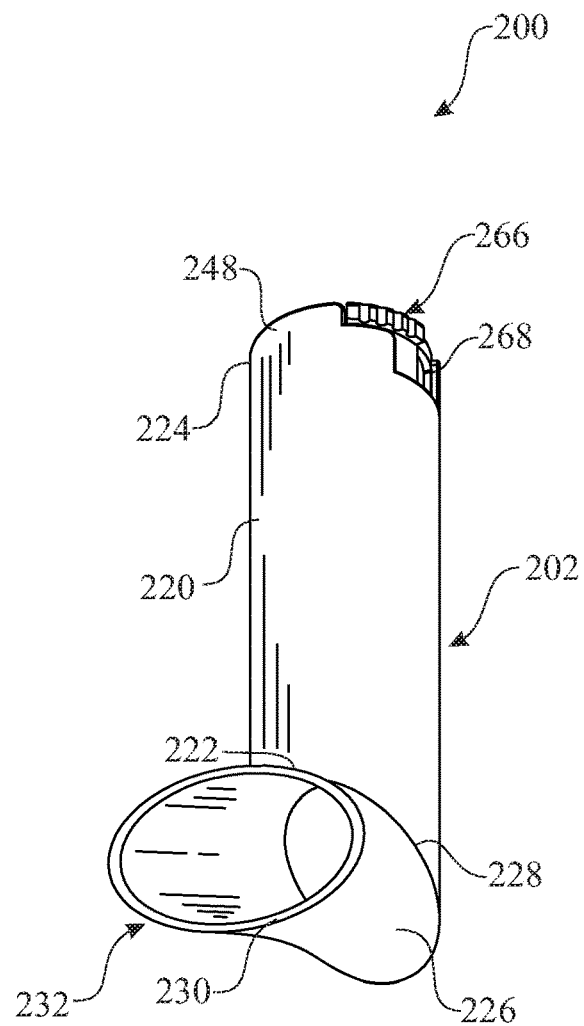
FIG. 8. presents an upper front isometric assembled view of an alternate exemplary embodiment of a hand-held dose-dispensing pressurized sprayer for an eye in accordance with aspects of the present invention.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Referring now to FIGS. 1-4, there is illustrated an exemplary embodiment of a hand-held dose-dispensing pressurized spray inhaler, generally designated 100, in accordance with aspects of the present invention. The inhaler 100 includes a housing 102 having an interior chamber 104, an aerosol canister 106 disposed in the interior chamber of the housing and having a canister body 108 and a movable valve stem 110 biased to extend from the canister body and retract toward the canister body to produce release of a dose of pressurized spray from the canister body through a dispensing end 112 of the valve stem 110, a fixture 114 stationarily holding or supporting the valve stem 110 relative to the housing 102, and an actuation mechanism 116 normally in a locked condition and being convertible to an unlocked condition. The actuation mechanism 116 fitted at least partially over the canister body 108 opposite from the valve stem 110 such that only the actuation mechanism together with the fixture 114 support the canister body in the interior chamber 104 of the housing 102 with a clearance gap 118 around and between the canister body and the housing and for movement relative to the housing and toward and away from the fixture. The actuation mechanism 116 provides a child restraint capability by requiring that a coordinated sequence of multiple unlocking actions be carried out to convert the actuation mechanism from the locked condition to the unlocked condition and move the canister body relative to the housing 102 and the valve stem 110 in a manner that releases the dose of pressurized spray from the dispensing end 112 of the valve stem and from the housing. Although the inhaler 100 primary purpose is to function with an aerosol canister, it is readily understood that the present invention could be used with a non-aerosol pump configuration (not presently shown).

The inhaler housing 102, which may be made out of metal, glass, plastic, or any series of suitable rigid materials includes a housing body 120 in the form of an elongated sidewall being cylindrical in shape and having a pair of opposite open ends 122, 124 with the interior chamber 104 of the housing extending between them. The housing 102 also includes a mouthpiece 126 on the housing body 120 at the one open end 122 thereof. The mouthpiece 126 is angularly affixed to, or merges at an angle from, the one open end 122 of the sidewall of the housing body 120, the angle being one selected to make the inhaler 100 easy and comfortable to use. By way of example but not limitation, the angle may be an obtuse one, slightly larger than a right angle. The mouthpiece 126 has a pair of opposite end openings 128, 130 and an interior passage 132 extending between them providing an extension of the interior chamber 104 of the housing 102. The mouthpiece 126 may be of substantially the same diameter size but of substantially shorter axial length than the housing body 120.

The canister body 108 of the inhaler aerosol canister 106 is of a size capable of fitting in the interior chamber 104 of the inhaler housing 102 with the clearance gap 118 of suitable size remaining around and between the canister body and the housing body elongated sidewall 120. The valve stem 110 of the aerosol canister 106 is biased to normally assume an extended position relative to one opposite end 136 of the canister body 108 so as to prevent release of the dose of pressurized spray from the aerosol canister 106. The valve stem 110 is depressible to retract it toward, and partially inserted into, the one opposite end 136 of the canister body 108 in order to produce release of the dose of pressurized spray from the aerosol canister 106 through the dispensing end 112 of the valve stem 110.

The inhaler fixture 114 that stationarily holds or supports the valve stem 110 relative to the housing 102 is affixed proximate at least one or both of the mouthpiece 126 and the housing body 120 adjacent to the one open end 122 thereof in alignment with the valve stem 110 of the aerosol canister 106. By way of example but not limitation, in FIG. 2 the fixture 114 is shown affixed on the mouthpiece adjacent to the one end opening 128 thereof and adjacent to one open end 122 of the housing body 120. The fixture 114 may be in the form of a tubular pedestal with the orifice 138 on a side thereof facing outwardly through the mouthpiece 126 and being aligned with the dispensing end 112 of the valve stem 110 of the aerosol canister 106 and a central passageway 140 leading through the tubular pedestal from the valve stem of the aerosol canister to the orifice.

The inhaler actuation mechanism 116 includes an end cap 142 having an endless side wall 144 of a cylindrical shape conforming to that of the housing body 120. The end cap side wall 144 has a pair of opposite ends 146, 148 and defines an interior cavity 150 extending between them. The end cap 142 is open at the side wall one end 146 and has an end wall 152 closing the other side wall end 148. The canister body 108 at its other opposite end 154 snugly fits through the one open side wall end 146 of the end cap 142 such that the presence of the circumferential portion of the end cap side wall 144 surrounding the canister body 108 and between the housing body 120 and the canister body defines the width of the clearance gap 118 around and between the canister body 108 and the housing body 120. The end cap 142 and the aerosol canister 106 therewith are capable of undergoing both rotational movement about, and axial movement along, a central axis 156 that extends lengthwise through the housing body 120 of the inhaler housing 102.

The inhaler actuation mechanism 116 also includes at least one notch 158, and preferably a pair of diametrically opposite notches 158, provided in an end edge 160 defining the other open end 124 of the housing body 120. Each notch 158 defines a locking edge portion 162 providing an upper limit stop and an unlocking edge portion 164 providing a lower limit stop adjacent to but spaced farther from the end edge 160 defining the other open end 124 of the housing body 120 than the locking edge portion 162 in a circumferential direction of rotation of the end cap 142 about the central axis 156.

The inhaler actuation mechanism 116 further includes at least one locking structure 166, and preferably a pair of diametrically opposite locking structures 166, formed proximate and protruding radially outward from the side wall 144 of the end cap 142 adjacent to the end wall 152 thereof. The circumferential arcuate length of the locking structure 166 is greater than that of the locking edge portion 162 but less than that of the unlocking edge portion 164. This means that once the end cap 142 and the aerosol canister 106 therewith have been rotated sufficiently to displace the locking structure 166 away from the locking edge portion 162 to overlie and bring into alignment with the unlocking edge portion 164, the end cap 142 and the aerosol canister 106 therewith can be moved in the direction parallel to the central axis 156 until the locking structure 166 engages the lower limit stop provided by the unlocking edge portion 164. Thus the lower limit stop provided by the unlocking edge portion 164 determines the maximum displacement of the end cap 142 and therefore of the canister body 108 of the aerosol canister 106 relative to its valve stem 110 and parallel to the central axis 156. This maximum displacement is designed to be sufficient to enable release of the dose of pressurized spray from the valve stem 110 of the aerosol canister 106. The locking structure 166 may take the form of a series of spaced ribs as shown or a single elongated rib.

The inhaler actuation mechanism 116 further includes an aperture 168 defined in the side wall 144 of the end cap 142 adjacent and circumferentially spaced about the side wall from one of the locking structures 166, as seen in FIGS. 1-5, and a yieldable locking member 170 that defines a normally outwardly-protruding push button 172 associated with the aperture 168 for enabling the inhaler actuation mechanism 110 to convert between the locked and unlocked conditions. In an exemplary form as best seen in FIGS. 3 and 4, the yieldable locking member 170 may have a ring-shaped configuration in the form of an arcuate-shaped segment 174 with the outwardly-protruding push button 172 integrally formed thereon and a pair of opposite ends 176, 178 being spaced apart by a short gap 180 compared to the circumferential length of the locking member segment 174. The normally outwardly-protruding push button 172 is formed on the locking member segment 174 adjacent to the one opposite end 176. The yieldable locking member 170 is installed within the side wall 144 of the end cap 142 between the end wall 152 of the end cap 142 and the other opposite end 154 of the canister body 108 such that the push button 172 normally projects through the aperture 168 in the side wall 144 of the end cap 142. The locking member segment 174 acts as a spring that biases the yieldable locking member segment 174 toward its expanded arcuate-shaped configuration that projects the push button 172 through the aperture 168 in the side wall 144 of the end cap 142 adjacent to a side edge portion 182 of the notch 158 that retains the inhaler actuation mechanism 116 at its locking condition due to interference created by the normally outwardly-protruding push button 172 with the notch side edge portion 182 which prevents the locking structure 166 to be rotated past and free of the upper limit stop of the locking edge portion 162.

Thus, the inhaler actuation mechanism 116 provides a child restraint capability by requiring that a coordinated sequence of multiple unlocking actions be carried out to convert the actuation mechanism from the locked condition to the unlocked condition. The coordinated sequence of multiple unlocking actions begins by depressing the push button 172 to displace it into the interior cavity 150 of the end cap 142 and thus remove it from the path of interference with the notch side edge portion 182 of the housing 102. Next, as the push button 172 is held depressed the end cap 142 is rotated about the central axis 156 of the housing 102 toward the notch side edge portion 182 of the housing 102 to thereby move the depressed push button past the inside of the notch side edge portion 182 of the housing 102 which concurrently slides the locking structure 166 sideways away from the upper limit stop of the notch locking edge portion 162 of the housing 102 into overlying spaced alignment with the lower limit stop of the notch unlocking edge portion 164 of the housing 102. Finally, the end cap 142 is depressed into the open end 124 of the housing 102 to axially move the canister body 108 of the aerosol canister 106 relative to the stationarily-held valve stem 110 of the aerosol canister 106 until the locking structure 166 makes contact with the lower limit stop of the notch unlocking edge portion 164 of the housing 102. It is considered that the average child would not be able to coordinate both of his or her hands so as to perform these or similar unlocking actions to move the canister body 108 relative to the housing 102 and the valve stem 110 in a manner that releases the dose of pressurized spray from the dispensing end 112 of the valve stem and from the housing.

The housing 102, the end cap 142, and the yieldable locking member 170 may be manufactured using any of the well known manufacturing processes known by those skilled in the art, including injection molding, vacuum forming, machining, and the like. Additionally, it is contemplated that the material selected to fabricate these components may be chosen based upon material properties that provide specific performance of each component for each respective function, such as biasing or spring force characteristics of yieldable locking member 170, rigidity for the end cap 142, and the like. It is also recognized that these components may be fabricated in different colors for any of a multitude of reasons. The housing 102 and the end cap 142 are preferably fabricated of the same material, which is preferably injection molded plastic, polypropylene, and the like. The yieldable locking member 170 can be fabricated of plastic, silicone, acetyl and the like, preferably fabricated of a material having a geometric memory. Different colors can be used to aid in locating the push button 172. Different colors can be utilized for color-coding features and functionality, and the like.

Referring now to FIG. 8, in another implementation, the inhaler 200 includes an inhaler housing 202 that has a housing body 220 in the form of an elongated sidewall being cylindrical in shape and having a pair of opposite ends 222, 224 with the interior chamber of the housing extending between them. The housing 202 also includes an eyepiece 226 on the housing body 220 at the one open end 222 thereof. The eyepiece 226 is angularly affixed to, or merges at an angle from, the one open end 222 of the sidewall of the housing body 220, the angle being one selected to make the inhaler 200 easy and comfortable to use. By way of example but not limitation, the angle may be an obtuse angle, slightly larger than a right angle. The eyepiece 226 has a pair of opposite end openings 228, 230 and an interior passage 232 extending between them providing an extension of the interior chamber of the housing 202. In a preferred embodiment, the eyepiece 226 has an oval-shaped orifice which allows for the direct administration of medication in an aerosol or non-aerosol form to an eye of a user. Although the preferred embodiment of the inhaler 200 is oval-shaped, it can be construed by one skilled in the art that any shape can be adapted to the inhaler 200 in order to administer a dosage of medication. Both the inhalers 100, 200 can be used right side up or upside down. For inverted use the inhaler may function with the exclusion of a dip-tube (valve system), only requiring a pump (or valve).

In another implementation (not shown), the child-resistant inhaler can be modified to provide a pressurized aerosol or any other kind of metered or non-metered dosages. The housing body may include a square-shaped, oval-shaped, or rectangular-shaped delivery member that is angularly affixed to, or merged at an angle from, the open end of the sidewall of the housing body of said inhaler, wherein each delivery member is intended to accommodate for the administration of a specific substance to be delivered to a user. For example, but not to be construed as limiting, an oval-shaped delivery member affixed to said inhaler body may be used to deliver an ophthalmic substance to a user's eye.

The above-described embodiments are merely exemplary illustrations of implementations set forth for a clear understanding of the principles of the invention. Many variations, combinations, modifications or equivalents may be substituted for elements thereof without departing from the scope of the invention. Therefore, it is intended that the invention not be limited to the particular embodiments disclosed as the best mode contemplated for carrying out this invention, but that the invention will include all the embodiments falling within the scope of the appended claims.

What is claimed is:

1. A hand-held dose-dispensing pressurized spray inhaler, comprising:

a housing having a housing body and a contiguous interior housing body surface defining an interior chamber extending between a housing body open top end and a housing body open lower end, said housing body open lower end transitioning to a mouthpiece having an open interior end and an opposite open exterior end, said mouthpiece interior end defining a mouthpiece interior opening contiguous with said housing body open lower end, the mouthpiece having a contiguous interior surface defining a mouthpiece interior chamber in fluid communication with the corresponding interior chamber of said housing body such that the interior chambers of said respective housing body and mouthpiece are in fluid communication with one another;

an aerosol canister disposed in said interior chamber of said housing body and having a canister body and a movable valve stem biased to extend away from said canister body but retractable into the canister body to effect the release of a volume of pressurized spray from an interior of said canister body through a dispensing end of said movable valve stem;

a tubular fixture extending vertically upwards from an interior surface of said mouthpiece in a direction toward said housing open top end, the tubular fixture having a contiguous sidewall defining a channel sized and shaped for stationarily supporting the aerosol canister moveable valve stem relative to the housing body, said tubular fixture defining a channel length greater than a corresponding length of said movable valve stem; and a child-resistant mechanical actuator subassembly normally in a locked position but convertible to an unlocked condition position, said mechanical actuator subassembly including a C-shaped yieldable locking member having an integral push button protruding outwardly from an exterior surface thereof beyond said housing body sidewall, said C-shaped yieldable locking member at least partially circumscribing an exterior surface of said canister body upper end opposite said valve stem such that only said mechanical actuator subassembly, together with said fix lure, support said canister body in the housing open interior to define a clearance gap around said canister body and extending between the exterior surface of said canister body and the interior surface of said housing body, the clearance gap enabling displacement of said canister body relative to said housing body in a direction along a common central axis of said movable valve stem and said tubular fixture, said child resistant mechanical actuator subassembly providing child restraint capability by requiring a coordinated sequence of multiple unlocking actions be carried out to convert said mechanical actuator subassembly from said locked position to said unlocked position to enable linear displacement of said canister body relative to said housing body and valve stem such that engagement of a canister body lower end against an upper edge of said tubular fixture causes retraction of said movable valve stem into said aerosol canister body to effect the release of a metered volume of pressurized spray through said valve stem from said housing body;

wherein said child-resistant mechanical actuator subassembly further comprises a unitary end cap disposed over both an upper end of said canister body and said C-shaped yieldable locking member such that said locking member separates a closed upper end of the unitary end cap from the upper end of the canister body, said integral push button protruding outwardly from said C-shaped yieldable locking member exterior surface seated within a first notch provided along an upper edge of said housing body, said unitary end cap including at least one arcuate locking structure protruding outwardly from an upper end thereof and seated within a corresponding arcuate second notch provided along said housing body upper edge, wherein said arcuate second notch has an arc length greater than a corresponding arc length of said locking structure.

2. An inhaler as recited in claim 1 wherein said fixture further comprises an open-ended tubular pedestal having an orifice extending completely through a sidewall thereof, a central passageway leading from said valve stem of said aerosol canister to said tubular pedestal orifice.

3. The inhaler of claim 1 wherein said fixture is a tubular pedestal having an orifice defined on a side thereof and a central passageway leading from said valve stem of said aerosol canister to said orifice.

* * * * *